(12) United States Patent
Towson et al.

(10) Patent No.: US 8,501,788 B2
(45) Date of Patent: Aug. 6, 2013

(54) PROCESS FOR RECOVERING FLUNIXIN FROM PHARMACEUTICAL COMPOSITIONS

(75) Inventors: James C. Towson, Flemington, NJ (US); Donal Coveney, Dublin (IE)

(73) Assignee: Intervet Inc., Summit, NJ (US)

( * ) Notice: Subject to any disclaimer, the term of this patent is extended or adjusted under 35 U.S.C. 154(b) by 250 days.

(21) Appl. No.: 12/747,761

(22) PCT Filed: Dec. 12, 2008

(86) PCT No.: PCT/US2008/086498
§ 371 (c)(1),
(2), (4) Date: Sep. 14, 2010

(87) PCT Pub. No.: WO2009/079345
PCT Pub. Date: Jun. 25, 2009

(65) Prior Publication Data
US 2010/0331376 A1    Dec. 30, 2010

Related U.S. Application Data

(60) Provisional application No. 61/116,330, filed on Nov. 20, 2008, provisional application No. 61/013,855, filed on Dec. 14, 2007.

(51) Int. Cl.
*A61K 31/44* (2006.01)
*C07D 213/02* (2006.01)

(52) U.S. Cl.
USPC .......................................... 514/352; 546/310

(58) Field of Classification Search
None
See application file for complete search history.

(56) References Cited

U.S. PATENT DOCUMENTS 5,965,735 A * 10/1999 Doran et al. .................. 546/310
2009/0017095 A1    1/2009 Barnouin et al.

FOREIGN PATENT DOCUMENTS

| EP | 2 229 149 B1 | | 3/2012 |
|---|---|---|---|
| WO | WO 93/13070 | * | 7/1993 |
| WO | 03/097054 A1 | | 11/2003 |

OTHER PUBLICATIONS

Yamini et al, Talanta, vol. 58, No. 5, Nov. 12, 2002, pp. 1003-1010.*
International Search Report for PCT/US2008/086498, Mar. 10, 2009.*

* cited by examiner

*Primary Examiner* — Zinna Northington Davis

(57) ABSTRACT

This invention is generally directed to a method for recovering flunixin and flunixin analogs from pharmaceutical compositions. The recovered flunixin and analogs can be, for example, reused to make new pharmaceutical compositions and thereby reduce the need and expense of manufacturing new flunixin and flunixin analogs.

13 Claims, No Drawings

PROCESS FOR RECOVERING FLUNIXIN FROM PHARMACEUTICAL COMPOSITIONS

This application is the United States national stage application of International Application No. PCT/US2008/086498 filed Dec. 12, 2008, which claims priority from U.S. Provisional Application No. 61/013,855 filed Dec. 14, 2007, and U.S. Provisional Application No. 61/116,330 filed Nov. 20, 2008.

FIELD OF THE INVENTION

The present invention relates generally to a new process for recovering flunixin and flunixin analogs from pharmaceutical compositions.

BACKGROUND OF THE INVENTION

Flunixin is a non-steroidal anti-inflammatory drug (NSAID) and cyclo-oxygenase inhibitor.

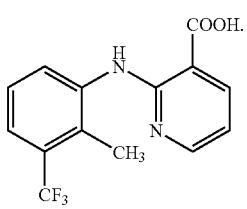

Formula I

Flunixin e is a potent analgesic, antipyretic, and anti-inflammatory drug that is used in veterinary medicine. Flunixin is 2-(2-methyl-3-trifluoromethylanilino) nicotinic acid or 2-[[2-Methyl-3-(trffluoromethyl)phenyl]amino]pyridine-3-carboxylic acid.

Flunixin meglumine is the active pharmaceutical ingredient in numerous drug products. Drug products containing flunixin are e.g. Resflor®, Banamine® Solution, Banamine Paste, Banamine Granules, Finadyne® (all Intervet/Schering Plough Animal Health).

Because flunixin is an expensive active pharmaceutical ingredient, a need exists for processes to recover flunixin from drug product manufacturing tailings, rejected or expired batches, or drug products that have been otherwise rendered unusable for technical, quality, manufacturing, or other reasons. In some embodiments, the recovered flunixin is reused to make new drug product. This reduces the need for (and, therefore, the expense associated with) destroying unusable drug product containing flunixin, and makes otherwise unusable flunixin available for use.

In addition to the economic benefits provided by the present invention, there are environmental benefits as well. Pharmaceutical waste (such as, for example, human medical or veterinary waste) containing rejected, expired, or unused batches of flunixin or flunixin analogs may enter water supplies, such as streams, oceans, and groundwater contaminated by drainage systems after disposal. The present invention provides methods to re-use flunixin or flunixin analogs that would normally be disposed of as pharmaceutical waste, thereby potentially reduce contamination of water supplies.

In some embodiments, the present invention provides an efficient and economical process for recovering flunixin or flunixin analogs from drug products.

SUMMARY OF THE INVENTION

It is an object of the present invention to provide a process for recovering flunixin or flunixin analogs from unusable pharmaceutical compositions.

In some embodiments, the present invention is directed to a process for recovering flunixin or flunixin analogs from a pharmaceutical composition comprising:
(a) obtaining a pharmaceutical composition comprising flunixin or flunixin analogs, and at least one auxiliary substance; and
(b) recovering the flunixin or flunixin analogs from the pharmaceutical composition by preferential dissolution.

In some embodiments, the present invention is directed to a process for preparing a pharmaceutical dosage form comprising:
(a) obtaining a pharmaceutical composition comprising flunixin or flunixin analogs, and at least one auxiliary substance;
(b) recovering the flunixin or flunixin analogs from the pharmaceutical composition by preferential dissolution; and
(c) formulating the recovered flunixin or flunixin analogs into a pharmaceutical dosage form comprising the flunixin or flunixin analogs, and at least one auxiliary substance.

In some embodiments, the present invention is directed to a process for purifying flunixin or flunixin analogs comprising:
(a) obtaining a pharmaceutical composition comprising flunixin or flunixin analogs, and at least one auxiliary substance;
(b) recovering the flunixin or flunixin analogs from the pharmaceutical composition by preferential dissolution; and
(c) purifying the flunixin or flunixin analogs to a purity of at least about 90%, at least about 95%, at least about 97%, or at least about 99%.

In some embodiments, the purified recovered flunixin or flunixin analogs are reformulated into a new dosage form.

In some embodiments, the present invention is directed to a process for recovering flunixin or flunixin analogs from a pharmaceutical composition comprising:
(a) obtaining a pharmaceutical composition comprising flunixin or flunixin analogs, and at least one auxiliary substance; and
(b) recovering the flunixin or flunixin analogs from the pharmaceutical composition by chromatography.

In some embodiments, the present invention is directed to a process for preparing a pharmaceutical dosage form comprising:
(a) obtaining a pharmaceutical composition comprising flunixin or flunixin analogs, and at least one auxiliary substance;
(b) recovering the flunixin or flunixin analogs from the pharmaceutical composition by chromatography; and
(c) formulating the recovered flunixin or flunixin analogs into a pharmaceutical dosage form comprising the flunixin or flunixin analogs, and at least one auxiliary substance.

In some embodiments, the present invention is directed to a process for purifying flunixin or flunixin analogs comprising:
(a) obtaining a pharmaceutical composition comprising flunixin or flunixin analogs, and at least one auxiliary substance;
(b) recovering the flunixin or flunixin analogs from the pharmaceutical composition by chromatography; and
(c) purifying the flunixin or flunixin analogs to a purity of at least about 90%, at least about 95%, at least about 97%, or at least about 99%.

In some embodiments, the purified recovered flunixin or flunixin analogs are reformulated into a new dosage form.

In some embodiments, the recovery of flunixin or a flunixin analog comprises a preferential dissolution of flunixin or a flunixin analog relative to the dissolution of at least one auxiliary substance.

In some embodiments, the recovery of the flunixin or a flunixin analog comprises a preferential dissolution of at least one auxiliary substance relative to flunixin or a flunixin analog.

In some embodiments, the recovery of flunixin or a flunixin analog comprises partitioning of at least one auxiliary substance in a first solvent from flunixin or a flunixin analog in a second solvent.

In some embodiments, this invention is directed to a method of conducting a pharmaceutical business comprising offering an incentive to a patient or healthcare provider to return an unused portion of a pharmaceutical dosage form.

In other embodiments, this invention is directed to a method of conducting a pharmaceutical business comprising:
(a) obtaining an unused portion of a pharmaceutical dosage form from a patient or healthcare provider; and
(b) recovering the active pharmaceutical ingredient from the unused portion of the pharmaceutical dosage form.

In some embodiments, this invention is directed to a method of conducting a pharmaceutical business comprising:
(a) preparing a pharmaceutical dosage form comprising an active pharmaceutical ingredient, and at least one auxiliary substance;
(b) distributing the pharmaceutical dosage form to a patient or healthcare provider;
(c) obtaining the unused portion of the pharmaceutical dosage form from the patient or healthcare provider; and
(d) recovering the active pharmaceutical ingredient from the unused portion of the pharmaceutical dosage form.

In some embodiments directed to methods of conducting a pharmaceutical business disclosed above, if not otherwise disclosed, an incentive (such as, for example, a monetary payment or rebate) is offered (to, for example, a patient or healthcare provider) to obtain the unused portion of the pharmaceutical dosage form.

In some embodiments, the present invention is directed to a method of preventing the contamination of the environment (such as, for example, water supplies and landfills) comprising:
(a) offering an incentive to a patient or healthcare provider to return an unused portion of a pharmaceutical dosage form; and
(b) obtaining the unused portion of the pharmaceutical dosage form from the patient or healthcare provider.

In such a method, the pharmaceutical dosage form generally will not be disposed of in a manner such that the active pharmaceutical ingredient can eventually contaminate water supplies or otherwise pollute the environment (such as, for example, in landfills).

In some embodiments, the present invention is directed to a process for recovering a compound of Formula II (or a pharmaceutically acceptable salt thereof) from a pharmaceutical composition by preferential dissolution of the auxiliary substances (such as, for example, pharmaceutically acceptable excipients or active pharmaceutical ingredients other than compounds of Formula II) relative to the dissolution of the active pharmaceutical ingredient.

Formula II compounds have the following structure:

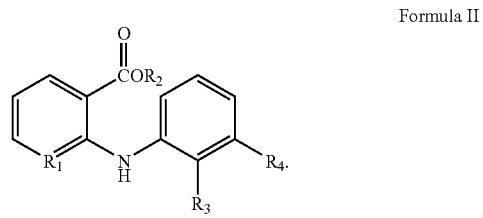

Formula II wherein:
$R_1$ is carbon, nitrogen, oxygen, sulfur or phosphorous;
$R_2$ is hydrogen, $C_{1-6}$ alkyl, $C_{3-8}$ cycloalkyl, benzyl, phenyl or phenyl alkyl where the phenyl ring may be substituted by one or two halogens, $C_{1-6}$ alkyl or $C_{1-6}$ alkoxy;
$R_3$ and $R_4$ are hydrogen, $C_{1-6}$ alkyl, $C_{1-6}$ haloalkyl, $C_{1-6}$ dihaloalkyl, $C_{1-6}$ trihaloalkyl, $CH_2Cl$, $CHCl_2$, $CCl_3$, $CH_2Br$, $CHBr_2$, $CBr_3$, $CH_2F$, $CHF_2$, $CF3$, $C_{3-8}$ cycloalkyl, $C_{3-8}$ cyclohaloalkyl, $C_{3-8}$ cyclodihaloalkyl, $C_{3-8}$ cyclotrihaloalkyl, $C_{2-6}$ alkenyl, $C_{2-6}$ alkynyl, $C_{1-6}$ alkoxy, $C_{1-6}$ aralkyl, $C_{2-6}$ aralkenyl, $C_{3-6}$ heterocyclic, benzyl, phenyl or phenyl alkyl where the phenyl ring may be substituted by one or two halogens, $C_{1-6}$ alkyl or $C_{1-6}$ alkoxy; $C_{1-6}$ alkylcarboxy, $C_{1-6}$ haloalkylcarboxy, $C_{3-8}$ cycloalkylcarboxy, $C_{2-6}$ alkenylcarboxy, $C_{2-6}$ alkenylcarboxy, $C_{2-6}$ alkynylcarboxy, $C_{1-6}$ alkoxycarboxy, $C_{3-6}$ heterocyclic carboxy, benzylcarboxy, phenylcarboxy, phenyl alkylcarboxy where the phenyl ring may be substituted by one or two halogens, $C_{1-6}$ alkyl or $C_{1-6}$ alkoxy In some embodiments, the recovery of flunixin or a flunixin analog from a pharmaceutical composition comprises:
(a) obtaining a pharmaceutical composition comprising flunixin or a flunixin analog, and at least one auxiliary substance;
(b) adding a solvent to the pharmaceutical composition that preferentially dissolves the auxiliary substances relative to the flunixin or flunixin analog to form a mixture;
(c) facilitating the dissolution of the auxiliary substances relative to the flunixin or flunixin analog in the mixture by performing at least one action selected from the group consisting of:
heating the mixture,
cooling the mixture,
adjusting the pH of the mixture,
adjusting the volume of the mixture,
separating a solvent phase in the mixture,
removing a solvent phase from the mixture, and
agitating the mixture;
(d) isolating the flunixin or flunixin analog from the mixture;
(e) optionally drying the flunixin or flunixin analog isolated from the mixture; and
(f) optionally purifying the flunixin or flunixin analog.

In some embodiments, the recovery of flunixin or a flunixin analog from a pharmaceutical composition comprises:
(a) obtaining a pharmaceutical composition comprising flunixin or a flunixin analog, and at least one auxiliary substance;
(b) adding a solvent to the pharmaceutical composition that preferentially dissolves the auxiliary substances relative to the flunixin or flunixin analog to form a mixture (the solvent may, for example, be selected from the group consisting of water, methanol, ethanol, isopropanol, propanol, butanol, t-butanol, pentanol, neo-pentanol, methylene chloride, chloroform, carbon tetrachloride, 1,2-dichloroethane, ethyl acetate, acetone, tetrahydrofuran, ether, dimethylsulfoxide, N,N-dimethylformamide, trifluoroethanol, and combinations thereof);

(c) facilitating the dissolution of the auxiliary substances relative to the flunixin or flunixin analog in the mixture by performing at least one action selected from the group consisting of:
  heating the mixture up to, and including, the boiling point of the solvent or solvent combination,
cooling the mixture to a temperature of from about −25° C. to about 25° C.,
adjusting the pH of the mixture to a pH of from about 1 to about 12, or, alternatively, to a pH of greater than about 10 or less than about 4,
adjusting the volume of the mixture,
separating a solvent phase in the mixture,
removing a solvent phase from the mixture, and
agitating the mixture;
(d) isolating the flunixin or flunixin analog from the mixture by centrifugation or filtration (including optionally washing the flunixin or flunixin analog with one or more solvents to further remove soluble auxiliary substances);
(e) optionally drying the flunixin or flunixin analog isolated from the mixture at a temperature of from about 50° C. to about 100° C.; and
(f) optionally purifying the flunixin or flunixin analog by recrystallization or chromatography.

In some embodiments, the invention is directed to a process for recovering a compound of Formula II from a pharmaceutical composition by preferential dissolution of the compound of Formula II relative to the dissolution of the auxiliary substances.

In some embodiments, the recovery of flunixin or a flunixin analog from a pharmaceutical composition comprises:
(a) obtaining a pharmaceutical composition comprising flunixin or a flunixin analog, and at least one auxiliary substance;
(b) adding a solvent to the pharmaceutical composition (this is also meant to encompass adding the pharmaceutical composition to the solvent in all embodiments herein) that preferentially dissolves the flunixin or flunixin analog relative to the auxiliary substances to form a mixture;
(c) facilitating the dissolution of the flunixin or flunixin analog relative to the auxiliary substances in the mixture by performing at least one action selected from the group consisting of:
heating the mixture,
cooling the mixture,
adjusting the pH of the mixture,
adjusting the volume of the mixture,
separating a solvent phase in the mixture,
removing a solvent phase from the mixture, and
agitating the mixture;
(d) removing undissolved auxiliary substances from the mixture;
(e) precipitating or crystallizing the flunixin or flunixin analog from the mixture (such as, for example, by reducing the solvent volume of the mixture);
(f) isolating the flunixin or flunixin analog from the mixture;
(g) optionally drying the flunixin or flunixin analog isolated from the mixture; and
(h) optionally purifying the flunixin or flunixin analog.

In some embodiments, the recovery of flunixin or a flunixin analog from a pharmaceutical composition comprises:
(a) obtaining a pharmaceutical composition comprising flunixin or a flunixin analog, and at least one auxiliary substance;
(b) adding a solvent to the pharmaceutical composition that preferentially dissolves the flunixin or flunixin analog relative to the auxiliary substances to form a mixture (the solvent may, for example, be selected from the group consisting of water, methanol, acetone, dimethylsulfoxide, dimethylformamide, dimethylacetamide, N-methylpyrrolidone, 2-pyrrolidone, trifluoroethanol, and combinations thereof);
(c) facilitating the dissolution of the flunixin or flunixin analog relative to the auxiliary substances in the mixture by performing at least one action selected from the group consisting of:
heating the mixture up to, and including, the boiling point of the solvent or solvent combination,
cooling the mixture to a temperature of from about −25° C. to about 25° C.,
adjusting the pH of the mixture to a pH of from about 1 to about 12, or, alternatively, to a pH of greater than about 10 or less than about 4,
adjusting the volume of the mixture,
separating a solvent phase in the mixture,
removing a solvent phase from the mixture, and
agitating the mixture;
(d) removing undissolved auxiliary substances from the mixture by centrifugation or filtration (including optionally washing the auxiliary substances with one or more solvents to further remove the flunixin or flunixin analog);
(e) reducing the solvent volume of the mixture by evaporation or distillation to precipitate or crystallize the flunixin or flunixin analog;
(f) isolating the flunixin or flunixin analog from the mixture by centrifugation or filtration (including optionally washing the flunixin or flunixin analog with one or more solvents to further remove soluble auxiliary substances);
(g) optionally drying the flunixin or flunixin analog isolated from the mixture at a temperature of from about 50° C. to about 100° C.; and
(h) optionally purifying the flunixin or flunixin analog by recrystallization or chromatography.

In some embodiments, the invention includes a process for recovering a compound of Formula II from a pharmaceutical composition by partitioning of the auxiliary substances in one solvent or solvent system from the compound of Formula II in a different solvent or solvent system.

In some embodiments, the recovery of flunixin or a flunixin analog from a pharmaceutical composition comprises:
(a) obtaining a pharmaceutical composition comprising flunixin or a flunixin analog, and at least one auxiliary substance;
(b) dissolving the pharmaceutical composition in at least two solvents to form a mixture, such that the flunixin or flunixin analog is preferentially partitioned in at least one solvent relative to the auxiliary substances;
(c) facilitating the dissolution of the flunixin or flunixin analog in the at least one solvent by performing at least one action selected from the group consisting of:
heating the mixture,
cooling the mixture,
adjusting the pH of the mixture,
adjusting the volume of the mixture,
separating a solvent phase in the mixture,
removing a solvent phase from the mixture, and
agitating the mixture;
(d) separating the at least one solvent containing the preferentially dissolved flunixin from the mixture;
(e) optionally repeating the immediate preceding steps b-d one or more times on the solvent containing the flunixin or flunixin analog to remove further auxiliary substance;

(f) optionally repeating the immediate preceding steps b-d one or more times on the remaining mixture containing the auxiliary substance to remove further flunixin or flunixin analog;

(g) precipitating or crystallizing the flunixin or flunixin analog from the at least one solvent by, for example, reducing the solvent volume;

(h) isolating the flunixin or flunixin analog from the at least one solvent (including optionally washing the flunixin or flunixin analog with one or more solvents to further remove soluble auxiliary substances);

(i) optionally drying the flunixin or flunixin analog isolated from the at least one solvent; and (j) optionally purifying the flunixin or flunixin analog.

In some embodiments, the recovery of flunixin or a flunixin analog from a pharmaceutical composition comprises:

(a) obtaining a pharmaceutical composition comprising flunixin or a flunixin analog, and at least one auxiliary substance;

(b) dissolving the pharmaceutical composition in at least two solvents to form a mixture, such that the flunixin or flunixin analog is preferentially partitioned in at least one solvent relative to the auxiliary substances (the flunixin-dissolving solvent may, for example, be selected from the group consisting of water, methanol, acetone, dimethylsulfoxide, dimethylformamide, trifluoroethanol, and combinations thereof);

(c) facilitating the dissolution of the flunixin or flunixin analog relative to the auxiliary substances in the mixture by performing at least one action selected from the group consisting of:
    heating the mixture up to, and including, the boiling point of the solvent or solvent combination,
    cooling the mixture to a temperature of from about −25° C. to about 25° C.,
    adjusting the pH of the mixture to a pH of from about 1 to about 12, or, alternatively, to a pH of greater than about 10 or less than about 4,
    adjusting the volume of the mixture, and
    agitating the mixture;

(d) separating the at least one solvent containing the preferentially dissolved flunixin from the mixture;

(e) optionally repeating the immediate preceding steps b-d one or more times on the solvent containing the flunixin or flunixin analog to remove further auxiliary substance;

(f) optionally repeating the immediate preceding steps b-d one or more times on the remaining mixture containing the auxiliary substance to remove further flunixin or flunixin analog;

(g) reducing the solvent volume of the mixture by evaporation or distillation to precipitate or crystallize the flunixin or flunixin analog;

(h) isolating the flunixin or flunixin analog from the mixture by centrifugation or filtration (including optionally washing the flunixin or flunixin analog with one or more solvents to further remove soluble auxiliary substances);

(i) optionally drying the flunixin or flunixin analog isolated from the mixture at a temperature of from about 50° C. to about 100° C.; and (j) optionally purifying the flunixin or flunixin analog by recrystallization or chromatography.

In some embodiments disclosed herein, the recovery of flunixin or a flunixin analog comprises dissolving the pharmaceutical composition in a suitable solvent or solvent system, injecting the dissolved pharmaceutical composition onto a chromatography column, separating flunixin and/or flunixin analogs from each other (if more than one is present) and at least one auxiliary substance by elution through the chromatography column with a suitable mobile phase, and collecting and isolating the separated flunixin or flunixin analog(s).

After the chromatographic recovery, the flunixin or flunixin analogue is optionally dried and/or purified. In some embodiments, the drying of the flunixin or flunixin analog is at a temperature of from about 50° C. to about 100° C., and the optional purifying is by recrystallization or by further chromatography.

By virtue of the present invention, Applicants have provided significant processing advantages by recovering the compound of Formula II from pharmaceutical compositions.

In some particularly preferred embodiments, flunixin is recovered from a pharmaceutical composition.

The recovery of the compounds of Formulas I-II from pharmaceutical compositions eliminates the expense associated with destroying unusable compositions. In some embodiments, the recovered compounds of Formulas I-II are reused in the manufacture of new pharmaceutical dosage forms thereby saving additional expense by eliminating the need to manufacture such compounds (such as, for example, flunixin). Additionally, the recovery of compounds of Formulas I-II eliminates the need to dispose of this pharmaceutical waste. This, in turn, may reduce contamination of the environment.

The present invention generally has the advantage of being an efficient, and economical process for recovering, and salvaging flunixin from pharmaceutical compositions.

The present invention encompasses situations wherein there is one auxiliary substance, as well as situations wherein there are more than one auxiliary substances, and it may be necessary to repeat the processes disclosed herein (in part or in full) to separate the flunixin or flunixin analog from the auxiliary substances. For example, a disclosed process may preferentially dissolve one auxiliary substance (such as, for example, an excipient) relative to another auxiliary substance, such as, for example, an additional active pharmaceutical ingredient. This may result in the precipitation of the flunixin or flunixin analog in addition to the precipitation of the other auxiliary substances such as, for example, an additional active pharmaceutical ingredient. In some embodiments, the resulting precipitate is then subjected to the same or different recovery process as disclosed herein, one or more times, to recover the flunixin or flunixin analog.

Further, some embodiments of the present invention include the additional step of determining the solubilities of some or all of the ingredients of the pharmaceutical composition. By determining the solubilities of ingredients in the composition, the necessary solvent or solvent systems can then be selected to preferentially dissolve, preferentially not dissolve, or partition a particular ingredient.

In some embodiments of the processes disclosed in this patent, flunixin or a flunixin analog is recovered from one pharmaceutical composition, and utilized in the manufacture of the same or a different pharmaceutical composition. For example, in some such embodiments, flunixin or a flunixin analog is recovered from a transdermal dosage form, and then incorporated into a transdermal or solid oral dosage form. In some embodiments, the unusable, and newly manufactured pharmaceutical compositions are independently selected from the group consisting of parenteral dosage forms, topical dosage forms, oral solid dosage forms, liquid dosage forms, granular dosage forms, suspension dosage forms, aerosol dosage forms, transdermal dosage forms, sustained or controlled released dosage forms, implant dosage forms, and powder dosage forms.

Further benefits of this invention will be apparent to one skilled in the art from reading this specification.

DETAILED DESCRIPTION OF PREFERRED EMBODIMENTS

This detailed description of preferred embodiments is intended only to acquaint others skilled in the art with the invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

In this patent (including the claims), the following terms are intended to be read as defined below unless otherwise indicated. These definitions (as well as other definitions found throughout this patent) apply to all forms of the defined term, including the singular, plural, active, and past tense forms, to the extent multiple forms exist.

The term "flunixin analog" means a compound of Formula II that is other than flunixin. The term "flunixin analog" also encompasses salts of the compounds of Formula II, including salts of flunixin. In general, such salts are preferably pharmaceutically acceptable. Especially preferred in flunixin meglumine.

The term "auxiliary substance" means any ingredient other than the active pharmaceutical ingredient intended to be recovered. Such ingredients may include, for example, excipients or additional active pharmaceutical ingredients. In some embodiments, the processes disclosed in this patent is utilized to recover two or more active pharmaceutical ingredients from a pharmaceutical composition. Such embodiments may necessitate the repetition of some or all of the disclosed steps one or more times.

The term "impurity" means an ingredient other than the active pharmaceutical ingredient intended to be recovered, and auxiliary substances. Impurities may include, for example, elemental material or degradation products such as dimers, hydroxylated compounds, ketones, oxides, aldol adducts, semiquinones, free radical peroxides, ether-linked adducts, and dehydrogenated compounds.

The term "excipients" means all pharmacologically inactive substances (such as solvents, carriers, buffers, fillers, dispersants, colorants, preservatives, anti-microbial agents, anti-oxidant agents, and any other substance that is not an impurity) in a pharmaceutical composition other than the active pharmaceutical ingredient(s).

The term "active pharmaceutical ingredient" is a pharmacologically active substance responsible for pharmacological activity of the drug product.

The term "pharmaceutical composition" is synonymous with the term "drug product", and means a combination of one or more active pharmaceutical ingredients with one or more excipient. The pharmaceutical composition can be a final pharmaceutical dosage form or an intermediate in the manufacture of a pharmaceutical dosage form. A "pharmaceutical dosage form" can be in the form of, for example, parenteral dosage forms, topical dosage forms, oral solid dosage forms, liquid dosage forms, granular dosage forms, suspension dosage forms, aerosol dosage forms, transdermal dosage forms, sustained or controlled released dosage forms, implant dosage forms, or powder dosage forms. The intermediate can be any composition utilized during the production of the dosage form, such as, for example, a free flowing powder from a tablet press or a solution of active pharmaceutical ingredient to be processed into a suitable parenteral dosage form.

The term "patient" is defined as any subject who receives medical or veterinary attention, care, or treatment, and includes both humans, and animals.

The term "healthcare provider" is defined as an organization or person who delivers health care to any patient. A "healthcare provider" may be, for example, a hospital, research laboratory, medical or clinical laboratory, physician, physician assistant, support staff, a nurse, pharmacist, therapist, psychologist, dentist, optometrist, psychiatrist, clinical psychologist, clinical social worker, psychiatric nurse, friend, family member, veterinarian, animal owner, or animal caregiver.

The term "chromatography" means a technique for separating mixtures of components by passing the component mixture dissolved in a suitable mobile phase through a stationary phase that separates the compound or compounds of interest such that they can be isolated.

The term "acetyl" means a $CH_3CO-$ radical.

The term "alcoholic solvent" includes $C_{1-10}$ monoalcohols (such as, for example, methanol, ethanol, and mixtures thereof), $C_{2-10}$ dialcohols (such as, for example, ethylene glycol), and $C_{1-10}$ trialcohols (such as, for example, glycerin). The term "alcoholic solvent" also includes such alcohols mixed with any suitable co-solvent (i.e., a second solvent added to the original solvent, generally in small concentrations, to form a mixture that has greatly enhanced solvent powers due to synergism). Such co-solvents include solvents that are miscible with the alcoholic solvent, such as, for example, $C_{4-10}$ alkanes, aromatic solvents (such as benzene, toluene, and xylenes), halobenzenes (such as, for example, chlorobenzene), ethers (such as, for example, diethylether, tert-butylmethylether, isopropylether, and tetrahydrofuran), and mixtures of any of the above co-solvents.

The phrase "adding one or more solvents to a pharmaceutical composition" also means adding a pharmaceutical composition to a solvent(s) and vice versa.

The term "purity" means that the active pharmaceutical ingredient is free or substantially free of auxiliary substances and/or free or substantially free of impurities such as, for example, degradation products or other non-auxiliary-substance impurities. The purity for each is independently at least about 90%, at least about 95%, at least about 97%, or at least about 99%. In some embodiments, the purity is at least about 99% with respect to auxiliary substances, and at least about 97% with respect to impurities.

The phrase "obtaining a pharmaceutical composition" means collecting pharmaceutical dosage forms to subject them to the processes disclosed herein. The collecting can be from, for example, manufacturing tailings, or rejected or expired batches of product.

The term "alkyl" means a saturated straight or branched hydrocarbon, such as methyl, ethyl, propyl, or sec-butyl. Alternatively, the number of carbons in an alkyl can be specified. For example, "$C_{1-6}$ alkyl" means an "alkyl" containing from 1 to 6 carbon atoms.

The term "$C_{2-6}$ alkenyl" means an unsaturated branched or unbranched hydrocarbon having at least one double carbon-carbon (—C═C—) bond, and containing from 2 to 6 carbon atoms. Example alkenyls include, without limitation, ethenyl, 1-propenyl, isopropenyl, 2-butenyl, 1,3-butadienyl, 3-pentenyl, 2-hexenyl, and the like.

The term "$C_{2-6}$ alkynyl" means an unsaturated branched or unbranched hydrocarbon having at least one triple carbon-carbon (—C≡C—) bond, and containing from 2 to 6 carbon atoms. Example alkynyls include, without limitation, ethynyl, 1-propynyl, 2-propynyl, 2-butynyl, 3-butynyl, 2-penten-4-ynyl, and the like.

The term "$C_{1-6}$ alkoxy" means an alkyl-O— group. Examples alkoxy groups include, without limitation, methoxy, ethoxy, propoxy (including n-propoxy and isopropoxy), t-butoxy, and the like.

The term "$C_{1-6}$ arylalkyl" means a $C_{1-6}$ alkyl substituted by an aryl that is any radical derived from an aromatic hydrocarbon by the removal of a hydrogen atom. The aryl is optionally substituted by halo or $C_{1-6}$ alkyl.

The term "$C_{2-6}$ arylalkenyl" means a $C_{2-6}$ alkenyl substituted by an aryl that is any radical derived from an aromatic hydrocarbon by the removal of a hydrogen atom. The aryl is optionally substituted by halo or $C_{1-6}$ alkyl.

The term "bromo" means the chemical element bromine.

The term "benzyl" means the univalent radical $C_6H_5CH_2$—, formally derived from toluene (i.e., methylbenzene).

The term "chloro" means the chemical element chorine.

The term "$C_{3-8}$ cycloalkyl" means a saturated cyclic hydrocarbon (i.e., a cyclized alkyl group) containing from 3 to 8 carbon atoms. Example cycloalkyls include, without limitation, cyclopropyl, cyclobutyl, cyclopentyl, cyclohexyl, and the like.

The term "$C_{3-8}$ halocycloalkyl" means a $C_{3-8}$ cycloalkyl substituted by one or more halo. When there is more than one halo, the halo may be the same or different. In some embodiments, the $C_{3-8}$ halocycloalkyl is "$C_{3-8}$ monohalocycloalkyl," i.e., $C_{3-8}$ cycloalkyl substituted by one halo. In some embodiments, the $C_{3-8}$ halocycloalkyl is "$C_{3-8}$ dihalocycloalkyl," i.e., $C_{3-8}$ cycloalkyl substituted by two halo. In some embodiments, the $C_{3-8}$ halocycloalkyl is "$C_{3-8}$ trihalocycloalkyl," i.e., $C_{3-8}$ cycloalkyl substituted by three halo.

The term "$C_{2-10}$ dialcohol" means an alcohol containing two hydroxyls, and from 2 to 10 carbon atoms.

The term "fluoro" means the chemical element fluorine.

The term "fluoromethylsulfonyl" means a $CH_2FSO_2$— radical.

The term "fluoromethylsulfoxy" means a $CH_2FSO$— radical.

The term "fluoromethylthio" means a $CH_2FS$— radical.

The term "halo" means fluoro, chloro, bromo, or iodo.

The term "$C_{1-6}$ haloalkyl" means a $C_{1-6}$ alkyl wherein one or more hydrogens are replaced by halo. When there is more than one halo, the halo may be the same or different. In some embodiments, the $C_{1-6}$ haloalkyl is "$C_{1-6}$ monohaloalkyl," i.e., $C_{1-6}$ alkyl substituted by one halo. In some embodiments, the $C_{1-6}$ haloalkyl is "$C_{1-6}$ dihaloalkyl," i.e., $C_{1-6}$ alkyl substituted by two halo. In some embodiments, the $C_{1-6}$ haloalkyl is "$C_{1-6}$ trihaloalkyl," i.e., $C_{1-6}$ alkyl substituted by three halo.

The term "halo substituted phenyl" means a phenyl substituted by halo.

The term "$C_{3-8}$ heterocyclyl" means a ring system radical wherein one or more of the ring-forming carbon atoms is replaced by a heteroatom, such as an oxygen, nitrogen, or sulfur atom, which include mono- or polycyclic (i.e., having 2 or more fused rings) ring systems as well as spiro ring systems. The ring system can contain from 3 to 8 carbon atoms, and can be aromatic or non-aromatic.

The term "iodo" means the chemical element iodine.

The term "methylsulfonyl" means a $CH_3SO_2$— radical.

The term "methylsulfoxy" means a $CH_3SO$— radical.

The term "methylthio" means a $CH_3S$— radical.

The term "$C_{1-10}$ monoalcohol" means an alcohol containing one hydroxyl, and from 1 to 10 carbon atoms.

The term "nitro" means a —$NO_2$ radical.

The term "phenyl" means the monovalent radical $C_6H_5$— of benzene, which is the aromatic hydrocarbon $C_6H_6$.

The term "$C_{1-6}$ phenylalkyl" means a $C_{1-6}$ alkyl substituted by phenyl.

The term "$C_{1-10}$ trialcohol" means an alcohol containing three hydroxyls, and from 1 to 10 carbon atoms.

The term "pharmaceutically acceptable" is used adjectivally to mean that the modified noun is appropriate for use in a pharmaceutical product. When it is used, for example, to describe a salt, it characterizes the salt as not being deleterious to the intended recipient to the extent that the deleterious effect(s) outweighs the benefit(s) of the salt.

Throughout the specification, and the appended claims, a given chemical formula or name shall encompass all stereo, and optical isomers, and racemates thereof, as well as mixtures in different proportions of the separate enantiomers, where such isomers and enantiomers exist, as well as pharmaceutically acceptable salts thereof, and solvates thereof such as for instance, hydrates. Isomers can be separated using conventional techniques, such as, for example, chromatography or fractional crystallization. The enantiomers can be isolated by separation of a racemic mixture, for example, by fractional crystallization, resolution or high-performance (or -pressure) liquid chromatography (HPLC). The diastereomers can be isolated by separation of isomer mixtures, for instance, by fractional crystallization, HPLC, or flash chromatography. The stereoisomers also can be made by chiral synthesis from chiral starting materials under conditions which will not cause racemization or epimerization, or by derivatization, with a chiral reagent. The starting materials, and conditions will be within the understanding of one skilled in the art. All stereoisomers are included within the scope of the invention.

A given chemical formula or name shall encompass all prodrugs. Prodrugs include but are not limited to, agents converted by esterase or DOPA decarboxylase to active agents, esters of active agents, and agents which are demethylated, dephosphorylated, deacetylated, or dehydrolyzed to active agents.

A given chemical formula or name shall also encompass all metabolites, such as, for example, hydroxylated metabolites.

In some embodiments, there is provided a process for recovering from a pharmaceutical composition by preferential dissolution of the auxiliary substances, a compound of Formula II (or a pharmaceutically acceptable salt thereof):

In some preferred embodiments, the compound is flunixin.

A. Preferential Dissolution of the Auxiliary Substances

One preferred process corresponding to the invention includes the following:

a) Adding one or more solvents to a pharmaceutical composition containing the compound of Formula II such that the auxiliary substances of the pharmaceutical composition are preferentially dissolved, and the compound of Formula II is preferentially undissolved. In some embodiments, the pharmaceutical composition is placed into a reaction vessel, and the one or more solvents are added. For purposes of the present invention, the term "reaction vessel" shall be understood to mean a container known to those of ordinary skill which is capable of holding the reactants, and allowing the recovery to proceed to completion. The size, and type of vessel will, of course, depend upon the size of the batch, and the specific reactants selected. Depending on the solubility of the auxiliary substances, a non limiting list of dissolving solvents are water, methanol, ethanol, isopropanol, propanol, butanol, t-butanol, pentanol, neo-pentanol, methylene chloride, chloroform, carbon tetrachloride, 1,2-dichloroethane, ethyl acetate, acetone, tetrahydrofuran, ether, dimethylsulfoxide, N,N-dimethylformamide, trifluoroethanol, or combinations thereof. In some embodiments, the auxiliary-substance-dissolving solvent is water, ethanol, isopropanol, propanol, butanol, t-butanol, pentanol, neo-pentanol, and combinations thereof. In some preferred embodiments, the auxiliary-substance-dissolving solvent is water. In some embodiments, the volume ratio of solvent to pharmaceutical composition is from about 1:1 to about 20:1. In some embodiments, the volume ratio of solvent (such as, for example, water) to drug product is from about 5:1 to about 10:1. The solvent can be added to the reaction vessel over any suitable time, such as, for example, over about 24 hours, over about 12 hours, or over about 3 hour. In some embodiments, water is added over about 6 hours.

b) Heating, cooling, adjusting the pH, adjusting the volume, adding one or more additional solvents, separating and/or removing different solvent phases, stirring, or agitating the mixture to facilitate the further dissolution of the auxiliary substances, and the insolubility of the compound of Formula II. In some embodiments, the mixture is heated up to the boiling point of the utilized solvent or solvents (or the boiling point of the mixture). In other embodiments, the mixture is cooled to a temperature of less than about 25° C., such as from about −25° C. to about 25° C., from about −15° C. to about 15° C., or from about −5° C. to about 5° C. In some embodiments, the temperature of the mixture is maintained at a temperature of from about −15° C. to about 30° C. or from about −20° C. to about 25° C. In some embodiments, the pH is adjusted with a base to a pH of, for example, greater than about 8, such as from about 8 to about 12 or from about 9 to about 11. In other embodiments, the pH is adjusted with an acid to a pH of less than about 5, such as to a pH of about 1. A non-limiting list of reagents suitable for the basic pH adjustment includes inorganic bases such as NaOH, KOH, $Na_2CO_3$, $K_2CO_3$, $NaHCO_3$, $KHCO_3$, or organic bases such as sodium methoxide, potassium methoxide, sodium ethoxide, potassium ethoxide, and combinations thereof. A non-limiting list of reagents suitable for the acidic pH adjustment includes inorganic acids such as HCl, $H_2SO_4$, $HNO_3$, $H_3PO_4$, organic acids such as methanesulfonic acid, acetic acid, trifluoroacetic acid, and combinations thereof. In some embodiments, the pH is adjusted to a neutral pH which is defined as a pH of from about 6 to about 8, by the addition of a base, an acid, or a buffer. A non-limiting list of buffers includes biological buffers such as tris(hydroxymethyl)methylamine, 2-{[tris(hydroxymethyl)methyl]amino}ethanesulfonic acid, piperazine-N,N'-bis(2-ethanesulfonic acid), N-(2-acetamido)-2-aminoethanesulfonic acid, and commercial buffers such as a combination of potassium dihydrogen phosphate, and disodium hydrogen phosphate. The volume of the mixture can be reduced by, for example, distillation of the solvent or solvents or by separation of the phases should a phase spit occur. The volume can be increased by addition of more solvent or of a co-solvent that further enhances the solubility of the auxiliary substances. Stirring or agitation can also enhance the solubility of the auxiliary substances. In some embodiments, the mixture is stirred or agitated for up to about 24 hours. In other embodiments, the mixture is stirred or agitated for from about 1 hour to about 10 hours.

c) Isolating the undissolved solids of the compound of Formula II, from the mixture (by, for example, filtration), and optionally washing with one or more solvents to further remove soluble auxiliary substances. In some embodiments, the undissolved compound of Formula II is isolated by centrifugation or filtration. In some embodiments, the isolated compound of Formula II is then washed with the same or different auxiliary-substance-dissolving solvent to further remove soluble auxiliary substances. Depending on the solubility of the auxiliary substances, a non-limiting list of wash solvents includes water, methanol, ethanol, isopropanol, propanol, butanol, t-butanol, pentanol, neo-pentanol, methylene chloride, chloroform, carbon tetrachloride, 1,2-dichloroethane, ethyl acetate, acetone, tetrahydrofuran, ether, dimethylsulfoxide, N,N-dimethylformamide, trifluoroethanol, and combinations thereof. In some embodiments, the auxiliary-substance-excipient-dissolving solvent is water, ethanol, isopropanol, propanol, butanol, t-butanol, pentanol, neo-pentanol, or combinations thereof. In some preferred embodiments, the auxiliary-substance-dissolving solvent is water. The volume of wash solvent used will depend on the relative solubility of the auxiliary substances, and the insolubility of the compound of Formula II. In some embodiments, the volume-to-weight ratio of wash solvent to the compound of Formula II is from about 0.1:1 to about 10:1 or from about 0.1:1 to about 3:1. In other embodiments, the ratio is from about 1 to about 5:1 or from about 1 to about 1.5:1.

d) If necessary, drying the crude recovered compound of Formula II. In some embodiments, the crude recovered compound of Formula II is used directly. In other embodiments, the crude recovered compound of Formula II is dried at, for example, a temperature of from about 50° C. to about 100° C. In other embodiments, the crude recovered compound of Formula II is dried at a temperature of from about 70° C. to about 90° C. The drying is performed for a suitable time (such as, for example, from about 1 to about 24 hours) to obtain a desired moisture content. In preferred embodiments, the moisture content is less than about 5%, or less than about 1%.

e) If necessary, purifying the crude recovered compound of Formula II by, for example, recrystallization or chromatography, to produce the purified compound of Formula II. In some embodiments, purifying the compound of Formula II involves using an alcoholic solvent such as a $C_{1-10}$ alkyl monoalcohol, a $C_{1-10}$ alkyl dialcohol, or a $C_{1-10}$ alkyl trialcohol (all optionally mixed with water) to form the purified compound of Formula II. A non-limiting list of $C_{1-10}$ monoalcohols includes methanol, ethanol, propanol, isopropanol, butanol, sec-butanol, t-butanol, pentanol, and a mixture thereof. A non-limiting list of $C_{1-10}$ dialcohols includes ethylene glycol, propylene glycol, butylene glycol, and a mixture thereof. A non-limiting example of a $C_{1-10}$ trialcohol is glycerin. In some embodiments of a process of the present invention, the $C_{1-10}$ monoalcohol for the purification comprises isopropanol. In some embodiments of a process of the present invention, the $C_{1-10}$ dialcohol of the purification comprises propylene glycol. In some embodiments of a process of the present invention, the $C_{1-10}$ trialcohol of the purification comprises glycerin. In some embodiments of a process of the present invention, the purification comprises using a mixture of alcohol and water. In some embodiments, the mixture comprises methanol, ethanol, propanol, isopropanol, butanol, sec-butanol, t-butanol, pentanol, ethylene glycol, propylene glycol, butylene glycol, glycerin, or a mixture thereof. In some embodiments, the alcohol, such as isopropanol, and water are present in a ratio from about 1:5 to about 5:1 (for example, about 1:1). In some embodiments, the alcohol comprises isopropanol, and the ratio of the isopropanol to water mixture is about 1:1. In some embodiments, the compound of Formula II, and the about 1:1 isopropanol, and water mixture have a weight-to-volume ratio of from about 1:1 and about 10:1. In some embodiments, the weight-to-volume ratio of the compound of Formula II to the isopropanol/water mixture is about 1:4.6.

In some embodiments of the purification, the compound of Formula II is dissolved in a mixture of about 1:1 isopropanol and water mixture such that the volume ratio of the compound of Formula II to the isopropanol/water mixture of about 1:4.6. The resulting mixture is heated to reflux. The resultant solution is clarified by filtration with active carbon and a filter, then cooled to a temperature of from about 10° C. to about 30° C. to obtain crystallized compound of Formula II that is pure. As used in this patent, the terms "pure" or "purified" means reduced levels of impurities, and improved color compared to un-purified compound. In some embodiments, the compound of Formula II is obtained to a purity level of at least about 90%, at least about 95%, at least about 97%, or at least about 99%. In some embodiments, the solution is cooled to a temperature of from about 20° C. to about 25° C. to crystallize the purified compound of Formula II from the solution. The purified compound of Formula II is isolated by filtration, and washed with 1:1 isopropanol, and water. In some embodiments, the volume-to-weight wash ratio of the isopropanol/water mixture to the compound of Formula II is from about 0.25 to about 1.5:1. In some embodiments, the wash ratio is from about 0.6 to about 0.7:1. The purified compound of Formula II is then dried at a temperature of from about 60 to about 90° C. In some embodiments, the purified compound of Formula II is dried at a temperature of from about 75 to about 85° C. The drying is continued for about 24 hours. In some embodiments, the drying is continued until the moisture content of the purified compound of Formula II is less than about 2%. In some embodiments, the drying is continued until the moisture content is less than about 0.5%. In preferred embodiments, the purified compound of Formula II crystallized from the solution is Flunixin.

B. Preferential Dissolution of the Flunixin or Flunixin Analogs

Another preferred process corresponding to the invention includes the following:

a) Adding one or more solvents to a pharmaceutical composition containing the compound of Formula II such that the compound of Formula II is preferentially dissolved, and the auxiliary substances are preferentially undissolved. In some such embodiments, the pharmaceutical composition is placed into a reaction vessel, and the solvent or solvents are added as disclosed above in section A. A non limiting list of dissolving solvents for the compound of Formula II include water, methanol, acetone, dimethylsulfoxide, dimethylformamide, dimethylacetamide, N-methylpyrrolidone, 2-pyrrolidone, trifluoroethanol, and combinations thereof. In some embodiments, the dissolving solvent for the compound of Formula II is water, methanol, acetone, and combinations thereof. In some preferred embodiments, the dissolving solvent for the compound of Formula II is methanol. In some embodiments, the volume ratio of solvent to pharmaceutical composition is from about 1:1 to about 20:1. In some embodiments, the volume ratio of methanol to drug product is from about 2:1 to about 8:1. The solvent can be added to the reaction vessel over any suitable time, such as, for example, over about 24 hours, over about 12 hours, or over about 3 hour. In some embodiments, methanol is added over about 6 hours.

b) Heating, cooling, adjusting the pH, adjusting the volume, adding one or more additional solvents, separating and/or removing different solvent phases, stirring, or agitating the mixture to facilitate the further dissolution of the compound of Formula II, and the insolubility of the auxiliary substances. In some embodiments, the mixture is heated up to the boiling point of the solvent or solvents utilized (or the boiling point of the mixture). In some embodiments, the mixture is cooled to a temperature of less than about 25° C., such as from about −25° C. to about 25° C., from about −15° C. to about 15° C., or from about −5° C. to about 5° C. In some embodiments, the temperature of the mixture is maintained at from about −15° C. to about 30° C. or from about −20° C. to about 25° C. In some embodiments, the pH is adjusted with a base to a pH of greater than about 8, such as from about 8 to about 12 or from about 9 to about 11. In some embodiments, the pH is adjusted with an acid to a pH of less than about 5, such as to a pH of about 1. A non-limiting list of reagents suitable for the basic pH adjustment includes inorganic bases such as NaOH, KOH, $Na_2CO_3$, $K_2CO_3$, $NaHCO_3$, $KHCO_3$, or organic bases such as sodium methoxide, potassium methoxide, sodium ethoxide, potassium ethoxide, and combinations thereof. A non-limiting list of reagents suitable for the acidic pH adjustment includes inorganic acids such as HCl, $H_2SO_4$, $HNO_3$, $H_3PO_4$, organic acids such as methanesulfonic acid, acetic acid, trifluoroacetic acid, and combinations thereof. In some embodiments, the pH is adjusted to a neutral pH which is defined as a pH of from about 6 to about 8, by the addition of a base, acid, or buffer. A non-limiting list of buffers includes biological buffers such as tris(hydroxymethyl)methylamine, 2-{[tris(hydroxymethyl)methyl]amino}ethanesulfonic acid, piperazine-N,N'-bis(2-ethanesulfonic acid), N-(2-acetamido)-2-aminoethanesulfonic acid, and commercial buffers such as a combination of potassium dihydrogen phosphate, and disodium hydrogen phosphate. The volume of the mixture can be reduced by, for example, distillation of the solvent or solvents or by separation of the phases should a phase spit occur. The volume can be increased by, for example, addition of more solvent or of a co-solvent that further enhances the solubility of the compound of Formula II. Stirring or agitation can also enhance the solubility of the compound of Formula II. In some embodiments, the mixture is stirred or agitated for up to about 24 hours. In some embodiments, the mixture is stirred or agitated for from about 1 to about 10 hours.

c) Removing the undissolved solids of the auxiliary substances, from the mixture by, for example, filtration. In some embodiments, the undissolved auxiliary substances are isolated by centrifugation or filtration. In some embodiments, the isolated auxiliary substances are then washed with the Formula-II-dissolving solvent or solvents or other solvents that further remove the soluble compound of Formula II. In some embodiments, the Formula-II-dissolving solvent is selected from the list disclosed above. The volume of wash solvent used will depend on the relative solubility of the compound of Formula II, and the insolubility of the auxiliary substances. In some embodiments, the volume-to-weight ratio of wash solvent to the auxiliary substances is from about 0.1:1 to about 10:1. In some embodiments, the ratio is from about 1 to about 3:1.

d) Precipitating or crystallizing the compound of Formula II by, for example, reducing the volume of solvent with cooling to a temperature of from about −25° C. to about 10° C. or by cooling to a temperature of from about −25° C. to about 10° C. In some embodiments, the cooling is to a temperature of from about −5° C. to about 5° C.

e) Isolating the compound of Formula II from the mixture using the techniques discussed above in section A.

f) If necessary, drying and/or purifying the crude recovered compound of Formula II as disclosed above in section A.

C. Preferential Dissolution by Partitioning of the Flunixin or Flunixin Analogs, and the Auxiliary Substances One preferred process corresponding to the invention includes the following:

a) Adding at least two solvents to a pharmaceutical composition containing the compound of Formula II such that the auxiliary substances of the pharmaceutical composition are preferentially partitioned in one solvent (or solvent system), and the compound of Formula II is preferentially partitioned in another solvent (or solvent system). In some embodiments, the pharmaceutical composition is placed into a reaction vessel as disclosed above in section A. Depending on the solubility of the auxiliary substances, a non limiting list of auxiliary-substance-dissolving solvents may include, for example, those solvents disclosed above in section A. Also, the solvents utilized to partition the compound of Formula II may, for example, be selected from those disclosed above in section B. In some embodiments, the solvents are added to the pharmaceutical composition in the ratios, and over the time periods discussed above in sections A, and B.

b) Heating, cooling, adjusting the pH, adjusting the volume, adding one or more additional solvents, stirring, or agitating the mixture to facilitate the further partitioning of the auxiliary substances, and the compound of Formula II in their respective solvent or solvent system. In some embodiments, the mixture is heated up to the boiling point of the mixture. In other embodiments, the mixture is cooled to a temperature of less than about 25° C., such as from about −25° C. to about 25° C., from about −15° C. to about 15° C., or from about −5° C. to about 5° C. In some embodiments, the temperature of the mixture is maintained at from about −15° C. to about 30° C. or from about −20° C. to about 25° C. In some embodiments, the pH is adjusted with a base to a pH of greater than about 8, such as from about 8 to about 12 or from about 9 to about 11. In some embodiments, the pH is adjusted with an acid to a pH of less than about 5, such as to a pH of about 1. A non-limiting list of reagents suitable for the basic pH adjustment includes inorganic bases such as NaOH, KOH, $NaCO_2$, $KCO_2$, $NaHCO_3$, $KHCO_3$, or organic bases such as sodium methoxide, potassium methoxide, sodium ethoxide, potassium ethoxide, and combinations thereof. A non-limiting list of reagents suitable for the acidic pH adjustment includes inorganic acids such as HCl, $H_2SO_4$, $HNO_3$, $H_3PO_4$, organic acids such as methanesulfonic acid, acetic acid, trifluoroacetic acid, and combinations thereof. In some embodiments, the pH is adjusted to a neutral pH which is defined as a pH of from about 6 to about 8, by the addition of a base, acid, or buffer. A non-limiting list of buffers includes biological buffers such as tris(hydroxymethyl)methylamine, 2-{[tris(hydroxymethyl)methyl]amino}ethanesulfonic acid, piperazine-N,N'-bis(2-ethanesulfonic acid), N-(2-acetamido)-2-aminoethanesulfonic acid, and commercial buffers such as a combination of potassium dihydrogen phosphate, and disodium hydrogen phosphate. The volume of the mixture may be reduced by, for example, distillation of the solvents or by separation of the phases should a phase spit occur. The volume may be increased by, for example, adding more solvent or of a co-solvent that further enhances the partitioning of the auxiliary substances, and the compound of Formula II. Stirring or agitation can also enhance the partitioning of the auxiliary substances, and the compound of Formula II. In some embodiments, the mixture is stirred or agitated for up to about 24 hours. In some embodiments, the mixture is stirred or agitated for about 1 to about 10 hours.

c) If necessary, further partitioning of the auxiliary substances, and the compound of Formula II by repetition of one or more of the steps disclosed above one or more times;

d) Separating the at least one solvent containing the preferentially dissolved compound of Formula II from the mixture;

e) Optionally repeating the immediate preceding steps one or more times on the solvent containing the partitioned compound of Formula II to remove further auxiliary substance;

f) Optionally repeating the immediate preceding steps one or more times on the remaining mixture containing the partitioned auxiliary substance to remove further the compound of Formula II;

g) Collecting the solvent or solvent system containing the partitioned compound of Formula II, and precipitating or crystallizing the compounds as disclosed above in Section A;

h) Isolating the undissolved solids of the compound of Formula II, from the mixture as disclosed above in Section A, including any further washing to remove additional auxiliary substances; and i) If necessary, drying and/or purifying the crude recovered compound of Formula II as disclosed above in Section A.

D. Recovery of Flunixin or Flunixin Analogs and/or Auxiliary Substances by Chromatography In some embodiments, the flunixin, flunixin analogs or auxiliary substances may be recovered using chromatography. The term "chromatography", as described in the *IUPAC Nomenclature for Chromatography, Pure & Appl. Chem.*, Vol. 65, No. 4, pp. 819-872, 1993, the disclosure of which is hereby incorporated by reference, means a method of separation in which the components to be separated are distributed between two phases, one of which is stationary (stationary phase) while the other (the mobile phase) moves in a definite direction. Methods of chromatography which may be utilized in the present invention include, for example, frontal chromatography, displacement chromatography, elution chromatography, column chromatography (such as, for example, packed column and open-tubular chromatography), planar chromatography (such as, for example, paper chromatography (PC), thin layer chromatography (TLC)), gas-liquid chromatography (GLC), gas-solid chromatography (GSC), liquid-liquid chromatography (LLC), liquid-solid chromatography (LSC), gas chromatography (GC), liquid chromatography (LC) (such as, for example, high performance or pressure liquid chromatography (HPLC)), simulated moving bed chromatography (SMB), supercritical-fluid chromatography (SFC), adsorption chromatography, partition chromatography, ion-exchange chromatography (IC), exclusion chromatography, affinity chromatography, reversed-phase chromatography, simulated moving bed chromatography (SMBC), normal-phase chromatography, isocratic analysis, gradient elution, stepwise elution, two-dimensional chromatography, multi-dimensional chromatography, isothermal chromatography, programmed-temperature chromatography, programmed-flow chromatography, programmed-pressure chromatography, reaction chromatography, pyrolysis-gas chromatography, post-column derivatization, and any combinations thereof.

In some embodiments, recovering flunixin or a flunixin analog from a pharmaceutical composition comprises:

(a) obtaining a pharmaceutical composition comprising flunixin or a flunixin analog, and at least one auxiliary substance;

(b) dissolving the pharmaceutical composition in a suitable solvent or solvent system;
(c) introducing (e.g., injecting) the dissolved pharmaceutical composition onto a chromatography column;
(d) separating the flunixin or flunixin analog from auxiliary substances by elution through the chromatography column with a suitable mobile phase;
(e) collecting, and combining the fraction or fractions containing the separated flunixin or flunixin analog;
(f) if necessary to further separate the flunixin or flunixin analog, subjecting the combined fraction or fractions containing the separated flunixin or flunixin analog to steps b-e above;
(g) isolating the flunixin or a flunixin analog by precipitation or crystallization as described above in Section A;
(h) optionally drying the isolated flunixin or flunixin analog; and
(i) optionally purifying the flunixin or flunixin analog.

In some embodiments, recovering flunixin or flunixin analog from a pharmaceutical composition comprises:
(a) obtaining a pharmaceutical composition comprising flunixin or flunixin analog, and at least one auxiliary substance;
(b) dissolving the pharmaceutical composition in a suitable solvent or solvent system (the solvent or solvent system may, for example, be selected from the group consisting of water, methanol, acetone, acetonitrile, dimethylsulfoxide, dimethylformamide, dimethylacetamide, trifluoroethanol, and combinations thereof);
(c) introducing (e.g., injecting) the dissolved pharmaceutical composition onto a chromatography column;
(d) separating the flunixin or flunixin analog from each other (if more than one is present), and the auxiliary substances by elution through a chromatography column containing a normal or reverse stationary phase such as, for example, silica, cyanosilica, aminosilica, octylsilane, butylsilane, octadecylsilane, diisopropyloctadecylsilane, or diisobutyloctadecylsilane with a suitable mobile phase such as an organic solvent, water, a buffered water solution, or combinations thereof;
(e) collecting, and combining the fraction or fractions containing the separated flunixin or flunixin analog;
(f) if necessary to further separate the flunixin or flunixin analog, subjecting the combined fraction or fractions containing the separated flunixin or flunixin analog to steps b-e above;
(g) isolating the flunixin or a flunixin analog by precipitation or crystallization as described above in Section A;
(h) optionally drying the isolated flunixin or flunixin analog as described above in Section A; and
(i) optionally purifying the flunixin or flunixin analog as described above in Section A.

E. Methods of Conducting a Pharmaceutical Business

In some embodiments directed to methods of conducting a pharmaceutical business as disclosed herein, a manufacturer obtains unused portions of pharmaceutical dosage forms from a patient or healthcare provider, and proceed to recover the active pharmaceutical ingredient contained therein. In some embodiments, the recovered active pharmaceutical ingredient is then recycled into new dosage forms.

The portions of pharmaceutical dosage forms that are unused may be due to any number of reasons, such as, for example, the medicine has expired or the patient has discontinued therapy due to intolerance, recovery from an ailment, or a change in dosage strength or drug therapy.

In preferred embodiments, an incentive is offered to the patient or healthcare provider to promote the return of the dosage form. In some embodiments, the incentive is, for example, a monetary payment, a rebate, a coupon, merchandise, or a voucher for merchandise.

In some embodiments, the original manufacturer obtains the unused portion of pharmaceutical dosage forms, or a third party obtains the unused portion of pharmaceutical dosage forms. In some such embodiments, the third party then recovers the active pharmaceutical agent from the dosage forms, and utilizes the recovered agent for resale or in their own manufacturing processes. In some embodiments, a clearinghouse is established which obtains unused portions of pharmaceutical active agents from multiple manufacturers, and sources.

In some embodiments, the original manufacturer or third party who obtains the unused portion of active pharmaceutical ingredient out-sources the recovery of the active pharmaceutical ingredient contained therein.

In some embodiments, the above disclosed methods are also utilized to decrease the disposal of unused portions of active pharmaceutical ingredients to reduce their disposal in, for example, drainage systems or landfills. This could potentially reduce the contamination of water sources (such as, for example streams, oceans, and groundwater) with pharmaceutical agents.

In addition to flunixin and flunixin analogs, the methods of conducting a pharmaceutical business can be applied to other active pharmaceutical ingredients, such as, for example, steroidal compounds (such as, for example, mometasone, betamethasone, or pharmaceutically acceptable salts thereof), antibiotics (such as, for example, florfenicol, moxifloxacin, ciprofloxacin, orbifloxacin, gentamicin, cephalonium, enraymicin, or pharmaceutically acceptable salts thereof), anthelmintics (such as, for example, netobimin, ivermectin, or pharmaceutically acceptable salts thereof), coccidiostats (such as, for example, diclazuril or pharmaceutically acceptable salts thereof), immunosuppressants (such as, for example, cyclosporine or pharmaceutically acceptable salts thereof), insecticides (such as, for example, emacectin, indoxacarb, or pharmaceutically acceptable salts thereof), anabolics (such as, for example, zeranol or pharmaceutically acceptable salts thereof), infertility agents (such as, for example, cloprostenol or pharmaceutically acceptable salts thereof) antihistamines (such as, for example, loratadine, desloratadine, or pharmaceutically acceptable salts thereof), beta agonists (such as, for example, albuterol, formoterol, or pharmaceutically acceptable salts thereof), antifungals, (such as, for example, clotrimazole, posaconazole, or pharmaceutically acceptable salts thereof), opioid derivatives (such as, for example, buprenorphine, naloxone, or pharmaceutically acceptable salts thereof), chemotherapeutic agents (such as, for example, temozolamide, doxorubicin, amifostine, or pharmaceutically acceptable salts thereof), anti-viral agents (such as, for example, ribavirin or pharmaceutically acceptable salts thereof), monoclonal antibodies (such as, for example, infliximab), anti-hyperlipidemics (such as, for example, ezetimibe or pharmaceutically acceptable salts thereof), non-steroidal antiinflammatory drugs (such as, for example tepoxalin or pharmaceutically acceptable salts thereof), interferons (such as, for example, peg-interferon alfa-2b), anti-coagulants (such as, for example, eptifibatide or pharmaceutically acceptable salts thereof), and vasodilators (such as, for example, nitroglycerin).

The words "comprise", "comprises", and "comprising" in this patent (including the claims) are to be interpreted inclusively rather than exclusively. This interpretation is intended to be the same as the interpretation that these words are given under United States patent law.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

EXAMPLES

The following preparative examples are representative of processes and compounds of the present invention. While the present invention has been described with specificity in accordance with some embodiments of the present invention, the following examples serve only to exemplify and illustrate the present invention, and are not intended to limit or restrict the effective scope of the present invention.

Example 1

Recovery of Flunixin from Resflor®

Resflor® is an Intervet/Schering-Plough Animal Health Corp. drug product that contains 300 mg Florfenicol, 27.4 mg Flunixin Meglumine, 250 mg of N-methyl-2-pyrrolidinone or 2-pyrrolidinonem, 10 mg of citric acid, 150 mg of propylene glycol and polyethylene glycol in 1 mL.

About 300 g of Resflor® is added over about 1 hour to a stirring solution of about 24 mL of concentrated ammonia in about 3 L of water heated to about 50° C. Additional concentrated ammonia can be added to ensure that the pH is about 9. The mixture is stirred and cooled to room temperature. The resulting precipated Florfenicol is removed by filtration. The filtrate is acidifed to about pH 4.5 with 10% $H_2SO_4$ then stirred for about another 1 hour. The resulting precipitated Flunixin is collected by filtration then dried to a moisture content of less than about 1% to yield about 4 g of crude Flunixin (100%).

Example 2

Recovery of Flunixin from Banamine®

Banamine® Solution is an Intervet/Schering Plough Animal Health drug product that contains 83 mg Flunixin Meglumine (equivalent to 50 mg Flunixin), 0.1 mg edetate disodium, 2.5 mg sodium formaldehyde sulfoxylate, 4.0 mg diethanolamine, 207.2 mg propylene glycol, 5.0 mg phenol, hydrochloric acid and water for injection diluted to 1 mL.

50% Aqueous citric acid solution is added to about 0.5 L of Banamine Solution while maintaining the temperature at less than 30° C. The resulting mixture was agitated for about 1 hour while continuing to maintain the temperature at less than 30° C. The precipitated Flunixin was collected by filtration and washed with 0.5 L of water, then dried at about 50-60° C. to a moisture content of less than 1% to yield about 23.5 g of crude Flunixin (94%)

Example 3

Recovery of Flunixin from Banamine Paste®

Banamine Paste® is an Intervet/Schering Plough Animal Health drug product that contains 83.0 mg Flunixin Meglumine (equivalent to 50 mg Flunixin), 12.0 mg carboxymethylcellulose sodium, 250.0 mg corn starch, 100.0 mg propylene glycol and 555.0 mg purified Water per gram of paste.

5 L of water is added to about 500 g of Banamine Paste while maintaining the temperature at less than 30° C. The resulting mixture was agitated for about 3 hours while continuing to maintain the temperature at less than 30° C. The resulting precipitate was removed by filtration. The filtered solids were washed with about 1 L of water and the pH of the filtrate was adjusted to 4-5 with aqueous citric acid solution (50%). The precipitated Flunixin was collected by filtration and washed with 0.5 L of water, then dried at about 50-60° C. to a moisture content of less than 1% to yield about 22.4 g of crude Flunixin (90%).

Example 4

Recovery of Flunixin from Banamine Granules®

Banamine Granules® is an Intervet/Schering Plough Animal Health drug product that contains 41.46 mg Flunixin Meglumine (equivalent to 25.0 mg Flunixin), 363.54 mg corn starch, 320.00 mg sucrose, 250.00 mg calcium phosphate, 20.00 mg povidone and 5.00 mg silicon dioxide per gram of granules.

5 L of water is added to about 500 g of Banamine Granules while maintaining the temperature at less than 30° C. The resulting mixture was agitated for about 3 hours while continuing to maintain the temperature at less than 30° C. The solids were removed by filtration. The filtered solids were washed with about 1 L of water and the pH of the combined filtrates was adjusted to 4-5 with aqueous citric acid solution. The precipitated Flunixin was collected by filtration and washed with 0.5 L of water, then dried at about 50-60° C. to a moisture content of less than 1% to yield crude Flunixin.

What is claimed is:

1. A process for preparing a pharmaceutical dosage form comprising flunixin or a flunixin analog, wherein the process comprises:

(a) obtaining a pharmaceutical composition comprising flunixin or a flunixin analog, and at least one auxiliary substance;

(b) recovering the flunixin or a flunixin analog from the pharmaceutical composition by preferential dissolution; and (c) formulating the flunixin or a flunixin analog into a pharmaceutical dosage form comprising the flunixin or a flunixin analog, and at least one auxiliary substance;

wherein the flunixin or the flunixin analog is purified to a purity of at least 90% and wherein the recovery of the flunixin comprises a preferencial dissolution of at least one auxiliary substance by a solvent relative to flunixin or the flunixin analog and wherein the solvent is selected from the group consisting of water, methanol, ethanol, isopropanol, propanol, butanol, t-butanol, pentanol, neo-pentanol, methylene chloride, chloroform, carbon tetrachloride, 1,2-dichloroethane, ethyl acetate, acetone, tetrahydrofuran, ether, dimethylsulfoxide, N,N-dimethylformamide, trifluoroethanol, and combinations thereof.

2. The process of claim 1, wherein:
the flunixin analog is a compound of Formula II or a pharmaceutically acceptable salt thereof:

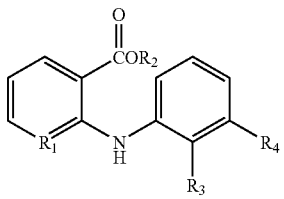

wherein:
$R_1$ is carbon, nitrogen, oxygen, sulfur or phosphorous;
$R_2$ is hydrogen, $C_{1-6}$ alkyl, $C_{3-8}$ cycloalkyl, benzyl, phenyl or phenyl alkyl where the phenyl ring may be substituted by one or two halogens, $C_{1-6}$ alkyl or $C_{1-6}$ alkoxy;
$R_3$ and $R_4$ are hydrogen, $C_{1-6}$ alkyl, $C_{1-6}$ haloalkyl, $C_{1-6}$ dihaloalkyl, $C_{1-6}$ trihaloalkyl, $CH_2Cl$, $CHCl_2$, $CCl_3$, $CH_2Br$, $CHBr_2$, $CBr_3$, $CH_2F$, $CHF2$, $CF3$, $C_{3-8}$ cycloalkyl, $C_{3-8}$ cyclohaloalkyl, $C_{3-8}$ cyclodihaloalkyl, $C_{3-8}$ cyclotrihaloalkyl, $C_{2-6}$ alkenyl, $C_{2-6}$ alkynyl, $C_{1-6}$ alkoxy, $C_{1-6}$ aralkyl, $C_{2-6}$ aralkenyl, $C_{3-6}$ heterocyclic, benzyl, phenyl or phenyl alkyl where the phenyl ring may be substituted by one or two halogens, $C_{1-6}$ alkyl or $C_{1-6}$ alkoxy; $C_{1-6}$ alkylcarboxy, $C_{1-6}$ haloalkylcarboxy, $C_{3-8}$ cycloalkylcarboxy, $C_{2-6}$ alkenylcarboxy, $C_{2-6}$ alkenylcarboxy, $C_{2-6}$ alkynylcarboxy, $C_{1-6}$ alkoxycarboxy, $C_{3-6}$ heterocyclic carboxy, benzylcarboxy, phenylcarboxy, phenyl alkylcarboxy where the phenyl ring may be substituted by one or two halogens, $C_{1-6}$ alkyl or $C_{1-6}$ alkoxy.

3. A process for purifying flunixin or a flunixin analog, wherein the process comprises:
(a) obtaining a pharmaceutical composition comprising flunixin or a flunixin analog, and at least one auxiliary substance;
(b) recovering the flunixin or a flunixin analog from the pharmaceutical composition by preferential dissolution; and
(c) purifying the flunixin or a flunixin analog to a purity of at least about 90%; and
wherein the recovery of the flunixin comprises a preferencial dissolution of at least one auxiliary substance by a solvent relative to flunixin or the flunixin analog and wherein the solvent is selected from the group consisting of water, methanol, ethanol, isopropanol, propanol, butanol, t-butanol, pentanol, neo-pentanol, methylene chloride, chloroform, carbon tetrachloride, 1,2-dichloroethane, ethyl acetate, acetone, tetrahydrofuran, ether, dimethylsulfoxide, N,N-dimethylformamide, trifluoroethanol, and combinations thereof.

4. The process of claim 3, wherein:
the active pharmaceutical ingredient comprises a compound of Formula II (or a pharmaceutically acceptable salt thereof):

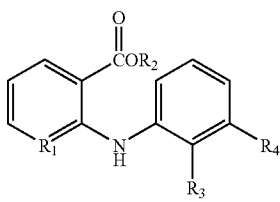

wherein:
$R_1$ is carbon, nitrogen, oxygen, sulfur or phosphorous;
$R_2$ is hydrogen, $C_{1-6}$ alkyl, $C_{3-8}$ cycloalkyl, benzyl, phenyl or phenyl alkyl where the phenyl ring may be substituted by one or two halogens, $C_{1-6}$ alkyl or $C_{1-6}$ alkoxy;
$R_3$ and $R_4$ are hydrogen, $C_{1-6}$ alkyl, $C_{1-6}$ haloalkyl, $C_{1-6}$ dihaloalkyl, $C_{1-6}$ trihaloalkyl, $CH_2Cl$, $CHCl_2$, $CCl_3$, $CH_2Br$, $CHBr_2$, $CBr_3$, $CH_2F$, $CHF_2$, $CF3$, $C_{3-8}$ cycloalkyl, $C_{3-8}$ cyclohaloalkyl, $C_{3-8}$ cyclodihaloalkyl, $C_{3-8}$ cyclotrihaloalkyl, $C_{2-6}$ alkenyl, $C_{2-6}$ alkynyl, $C_{1-6}$ alkoxy, $C_{1-6}$ aralkyl, $C_{2-6}$ aralkenyl, $C_{3-6}$ heterocyclic, benzyl, phenyl or phenyl alkyl where the phenyl ring may be substituted by one or two halogens, $C_{1-6}$ alkyl or $C_{1-6}$ alkoxy; $C_{1-6}$ alkylcarboxy, $C_{1-6}$ haloalkylcarboxy, $C_{3-8}$ cycloalkylcarboxy, $C_{2-6}$ alkenylcarboxy, $C_{2-6}$ alkenylcarboxy, $C_{2-6}$ alkynylcarboxy, $C_{1-6}$ alkoxycarboxy, $C_{3-6}$ heterocyclic carboxy, benzylcarboxy, phenylcarboxy, phenyl alkylcarboxy where the phenyl ring may be substituted by one or two halogens, $C_{1-6}$ alkyl or $C_{1-6}$ alkoxy.

5. The process of claim 1, wherein the pharmaceutical composition of step (a) comprises a pharmaceutical dosage form.

6. The process of claim 5, wherein the pharmaceutical composition comprises a pharmaceutical dosage form selected from the group consisting of parenteral dosage forms, topical dosage forms, oral solid dosage forms, liquid dosage forms, granular dosage forms, suspensions, aerosol dosage forms, transdermal dosage forms, sustained release dosage forms, controlled released dosage forms, implant dosage forms, and powder dosage forms.

7. The process of claim 1, wherein the pharmaceutical composition of step (a) comprises an intermediate in the production of a pharmaceutical dosage form.

8. The process of claim 1, wherein the auxiliary substance of the pharmaceutical composition comprises a substance selected from the group consisting of pharmaceutically acceptable excipients, additional active pharmaceutical ingredients, and a combination thereof.

9. The process of claim 1, wherein the preferential dissolution of the recovery comprises partitioning of at least one auxiliary substance in a first solvent from the flunixin or a flunixin analog in a second solvent.

10. A process for recovering flunixin or a flunixin analog from a pharmaceutical composition, wherein the process comprises:
(a) obtaining a pharmaceutical composition comprising flunixin or a flunixin analog, and at least one auxiliary substance;
(b) adding a solvent to the pharmaceutical composition that preferentially dissolves the auxiliary substances relative to the flunixin or flunixin analog to form a mixture;
(c) facilitating the dissolution of the auxiliary substances relative to the flunixin or flunixin analog in the mixture by performing at least one action selected from the group consisting of:
heating the mixture,
cooling the mixture,
adjusting the pH of the mixture,
adjusting the volume of the mixture,
separating a solvent phase in the mixture,
removing a solvent phase from the mixture, and
agitating the mixture;
(d) isolating the flunixin or flunixin analog from the mixture;
(e) drying the flunixin or flunixin analog isolated from the mixture; and (f) purifying the flunixin or flunixin analog
wherein the flunixin or the flunixin analog is purified to a purity of at least 90% and wherein the recovery of the flunixin comprises a preferencial dissolution of at least one auxiliary substance by a solvent relative to flunixin or the flunixin analog and wherein the solvent is selected from the group consisting of water, methanol, ethanol, isopropanol, propanol, butanol, t-butanol, pentanol, neo-pentanol, methylene chloride, chloroform, carbon tetrachloride, 1,2-dichloroethane, ethyl acetate, acetone, tetrahydrofuran, ether, dimethylsulfoxide, N,N-dimethylformamide, trifluoroethanol, and combinations thereof.

11. The process of claim 10, wherein the process comprises:
   (a) obtaining a pharmaceutical composition comprising flunixin or a flunixin analog, and at least one auxiliary substance;
   (b) adding a solvent to the pharmaceutical composition that preferentially dissolves the auxiliary substances relative to the flunixin or flunixin analog to form a mixture;
   (c) facilitating the dissolution of the auxiliary substances relative to the flunixin or flunixin analog in the mixture by performing at least one action selected from the group consisting of:
      heating the mixture to boiling,
      cooling the mixture to a temperature of from about −25° C. to about 25° C.,
      adjusting the pH of the mixture to a pH of greater than about 10 or less than about 4,
      adjusting the volume of the mixture,
      separating a solvent phase in the mixture,
      removing a solvent phase from the mixture, and
      agitating the mixture;
   (d) isolating the flunixin or flunixin analog from the mixture by centrifugation or filtration;
   (e) drying the flunixin or flunixin analog isolated from the mixture at a temperature of from about 50° C. to about 100° C.; and
   (f) purifying the flunixin or flunixin analog by recrystallization.

12. The process of claim 9, wherein the partitioning of the auxiliary substances in a first solvent from the flunixin or flunixin analog in a second solvent comprises:
   (i) dissolving the pharmaceutical composition in at least two solvents to form a mixture, such that the flunixin or flunixin analog is preferentially dissolved in at least one solvent relative to the auxiliary substances;
   (ii) facilitating the dissolution of the flunixin or flunixin analog in the at least one solvent by performing at least one action selected from the group consisting of:
      heating the mixture,
      cooling the mixture,
      adjusting the pH of the mixture,
      adjusting the volume of the mixture,
      separating a solvent phase in the mixture,
      removing a solvent phase from the mixture, and
      agitating the mixture;
   (iii) separating the at least one solvent containing the preferentially dissolved flunixin from the mixture;
   (iv) reducing the solvent volume of the at least one solvent to precipitate or crystallize the flunixin or flunixin analog; and
   (v) isolating the flunixin or flunixin analog from the at least one solvent.

13. The process of claim 12, wherein the process comprises:
   (a) obtaining a pharmaceutical composition comprising flunixin or a flunixin analog, and at least one auxiliary substance;
   (b) adding a solvent to the pharmaceutical composition that preferentially partitions the flunixin or flunixin analog relative to the auxiliary substances to form a mixture, wherein:
   the solvent is selected from the group consisting of water, methanol, acetone, dimethylsulfoxide, dimethylformamide, dimethylacetamide, N-methylpyrrolidone, 2-pyrrolidone, trifluoroethanol, and combinations thereof;
   (c) facilitating the dissolution of the flunixin or flunixin analog relative to the auxiliary substances in the mixture by performing at least one action selected from the group consisting of:
      heating the mixture to up to, and including, the boiling point of the solvent or solvent combination,
      cooling the mixture to a temperature of from about −25° C. to about 25° C.,
      adjusting the pH of the mixture to a pH of from about 1 to about 12,
      adjusting the volume of the mixture,
      separating a solvent phase in the mixture,
      removing a solvent phase from the mixture, and
      agitating the mixture;
   (d) separating the at least one solvent containing the preferentially dissolved flunixin from the mixture;
   (e) reducing the solvent volume of the mixture by evaporation or distillation to precipitate or crystallize the flunixin or flunixin analog;
   (f) isolating the flunixin or flunixin analog from the mixture by centrifugation or filtration;
   (g) drying the flunixin or flunixin analog isolated from the mixture at a temperature of from about 50° C. to about 100° C.; and
   (h) purifying the flunixin or flunixin analog by recrystallization.

* * * * *